United States Patent [19]

Krog et al.

[11] Patent Number: 6,045,782
[45] Date of Patent: *Apr. 4, 2000

[54] TRANSFER RESISTANT COSMETIC STICK COMPOSITION WITH SEMI-MATTE FINISH

[75] Inventors: Ann Marshall Krog, Red Bank, N.J.; Salvatore Joseph Barone, Staten Island; Natividad R. Jose, Jamacia, both of N.Y.; Gina Alyse McLaughlin, Somerset, N.J.

[73] Assignee: Revlon Consumer Products Corporation, New York, N.Y.

[ * ] Notice: This patent is subject to a terminal disclaimer.

[21] Appl. No.: 09/260,828

[22] Filed: Mar. 2, 1999

Related U.S. Application Data

[63] Continuation of application No. 08/992,464, Dec. 27, 1997, Pat. No. 5,945,092, which is a continuation of application No. 08/552,667, Nov. 3, 1995, Pat. No. 5,725,845.

[51] Int. Cl.[7] .................................................. A61K 7/27
[52] U.S. Cl. .............................. 424/64; 424/63; 424/401; 424/DIG. 5
[58] Field of Search ................................ 424/63, 64, 401, 424/DIG. 5

[56] References Cited

U.S. PATENT DOCUMENTS

| | | | |
|---|---|---|---|
| 5,244,665 | 9/1993 | Matrj et al. ............................. | 424/401 |
| 5,505,937 | 4/1996 | Catrogiovanni et al. ................ | 424/64 |
| 5,725,845 | 3/1998 | Krog et al. .............................. | 424/64 |

*Primary Examiner*—Jyothsna Venkat
*Attorney, Agent, or Firm*—Julie Blackburn

[57] ABSTRACT

An anhydrous cosmetic stick composition with improved transfer resistance comprising, by weight of the total composition:
a) 10–70% of a volatile solvent
b) 0.1–40% of a polymeric organosiloxane emulsifier containing at least one hydrophilic radical and at least one lipophilic radical.

5 Claims, No Drawings

TRANSFER RESISTANT COSMETIC STICK COMPOSITION WITH SEMI-MATTE FINISH

This is a continuation of application Ser. No. 08/992,464, filed Dec. 27, 1997 now U.S. Pat. No. 5,945,092, which is a continuation of patent application Ser. No. 08/552,667 filed Nov. 3, 1995 (now U.S. Pat. No. 5,725,845).

TECHNICAL FIELD

The invention is in the field of cosmetic compositions for application to skin and lips.

BACKGROUND OF THE INVENTION

Cosmetic compositions are generally defined as compositions suitable for application to the human body. Pigmented cosmetic compositions such as makeup, blush, lipstick, and eyeshadow are used to color the skin and lips, or to moisturize, hide wrinkles, and the like. Since color is one of the most important reasons for wearing cosmetics, color containing cosmetics must be very carefully formulated to provide maximum wear and effect.

One of the long standing problems with makeups such as face makeup, lipstick, mascara, and the like, is the tendency of the cosmetic to blot or transfer from the skin or lashes onto other surfaces such as glassware, silverware, skin, or clothing. This not only creates soiling, but forces the cosmetic user to reapply the cosmetic at fairly short intervals.

Cosmetic compositions with improved transfer resistance are disclosed in a previous patent application entitled "Cosmetic Compositions With Improved Transfer Resistance", filed by Applicants' assignee as U.S. Ser. No. 990,716 on Dec. 15, 1992, now abandoned which is hereby incorporated by reference. However, these transfer resistant cosmetic compositions can have a matte texture on the skin and lips.

However, some women prefer lipsticks that have a slightly glossy finish (referred to as semi-matte). In general, the ingredients that can be added to matte transfer resistant lipsticks to enhance gloss and provide a semi-matte finish have a tendency to compromise transfer resistance.

It has been unexpectedly discovered that cosmetic compositions containing the combination of a volatile solvent with a polymeric organosiloxane emulsifier that is miscible or soluble in the volatile solvent and has a lipophilic portion and a hydrophilic portion provides cosmetic compositions that have excellent transfer resistance, as well as providing a semi-matte finish when applied to skin.

An object of this invention is to formulate cosmetic compositions, particularly lipsticks, with long lasting adherence to skin that provides a semi-matte finish when applied to skin.

Another object of this invention is to formulate a transfer resistant cosmetic composition that provides a semi-matte finish, that, once applied to skin, resists transfer to glass, clothing, other skin, or utensils.

SUMMARY OF THE INVENTION

The invention is directed to a transfer resistant anhydrous cosmetic stick composition comprising, by weight of the total composition:
a) 10–70% of a volatile solvent having a viscosity of 0.5 to 25 centistokes at 25° C., and
b) 0.1–40% of a polymeric organosiloxane emulsifier containing at least one hydrophilic radical or portion, and at least one lipophilic radical or portion.

The invention is also directed to a method for providing a cosmetic stick composition with transfer resistance and a semi-matte finish when applied to skin, comprising adding to said composition the combination of a volatile solvent and a polymeric organosiloxane emulsifier that has at least one lipophilic radical or portion and at least one hydrophilic radical or portion.

DETAILED DESCRIPTION

The term "stick" refers to cosmetic compositions having a consistency such that they can be molded into the form of a stick—for instance by being heated until molten and then poured into a mold and cooled. Also included within the definition of "stick" are anhydrous compositions of the invention that are capable of being formed into sticks, but are poured into pans or other types of cake or cream forms to deliver certain consumer benefits. For example, an eyeshadow composition in accordance with the invention may be molded in the stick form, but it may be desired to pour it into a pan because this container is more desireable from a consumer standpoint.

The term "anhydrous" means that the composition contains no more than about 5 percent, more particularly about 1 to 2 percent by weight or less of water, or more preferably, that water is not intentionally added to the cosmetic composition of the invention.

The Volatile Solvent

The volatile solvent component of the composition is a liquid, and enables easy formulation of the cosmetic stick of the invention. When the cosmetic stick product of the invention is applied to skin or lips, the volatile solvent of the invention must be capable of flashing off to leave the other ingredients in the stick on the skin. The composition of the invention comprises 10–70%, preferably 20–65%, and most preferably 25–60% of a volatile solvent. The volatile solvent generally has a viscosity of 0.5 to 25 centistokes at 25° C. Suitable volatile solvents include linear silicones, cyclic silicones, paraffinic hydrocarbons, or mixtures thereof.

Cyclic silicones (or cyclomethicones) are of the general formula:

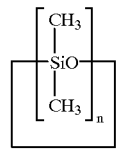

where n=3–7.

Linear volatile silicones in accordance with the invention have the general formula:

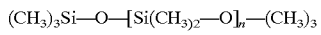

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as the volatile solvent are various straight or branched chain paraffinic hydrocarbons having 8 to 40 carbon atoms, more preferably 10–20 carbon atoms. Suitable hydrocarbons include decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 160 to 180 and a boiling point range of 105 to 320 degrees C., and a viscosity of less than 20 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. The volatile solvent may be a mixture of volatile silicones and paraffinic hydrocarbons if desired.

The Organosiloxane Emulsifier

Organosiloxane emulsifiers in accordance with the invention have been traditionally used in stabilizing cosmetic water and oil emulsions such as creams, lotions, and the like. It has unexpectedly been discovered that combining an organosiloxane emulsifier (surfactant) with a volatile solvent in an anhydrous cosmetic stick composition provides a stick that is not only transfer resistant when applied to skin or lips, but at the same time provides a semi-matte finish on the skin or lips. The semi-matte finish is achieved without substantially compromising transfer resistance. In addition, the cosmetic has a moist and comfortable feel on the skin or lips.

The composition of the invention preferably comprises 0.1–40%, more preferably 0.5–20%, and most preferably 1–15% of the polymeric organosiloxane emulsifier containing at least one lipophilic radical or portion and at least one hydrophilic radical or portion. Organosiloxane emulsifiers suitable for use in the compositions of the invention can be identified as those which, when combined with organic and inorganic pigments, and incorporated into an anhydrous stick composition provide a homogeneous single phase product. The polymeric organosiloxane used in the invention may be a liquid or solid at room temperature. The polymeric organosiloxane is generally a water-in-oil or oil-in-water type surfactant which is preferably nonionic, having an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w/M_o$$

where $M_w$ is the molecular weight of the hydrophilic group portion and $M_o$ is the molecular weight of the lipophilic group portion.

The term "organosiloxane polymer" means a polymer containing a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxypolypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxypolypropyleneoxy, or mixtures thereof The $C_{1-40}$ alkyl may be non-interrupted, or interrupted by one or more oxygen atoms, a benzene ring, amides, esters, or other functional groups.

The polymeric organosiloxane emulsifier used in the invention may have any of the following general formulas: ti $M_xQ_y$, or $$M_xT_y, \text{ or}$$

$$MD_xD'_yD''_zM$$

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof T is a trifunctional siloxy unit having the empirical formula $RR'SiO_{1.5}$ or $RRSiO_{1.5}$. Q is a quadrifunctional siloxy unit having the empirical formula $SiO_2$, and D, D', D'', x, y, and z are as set forth below, with the proviso that the compound contains at least one hydrophilic radical and at least one lipophilic radical. Examples of emulsifiers used in the compositions of the invention are of the general formula:

$$MD_xD'_yD''_zM$$

wherein the trimethylsiloxy endcap unit is unsubstituted or mono-substituted, wherein one methyl group is substituted with a lipophilic radical or a hydrophilic radical. Examples of such substituted trimethylsiloxy endcap units include $(CH_3)_2HPSiO$, $(CH_3)_2LPSiO$, $(CH_3)_2CH_2HPSiO$, $(CH_3)_2CH_2LPSiO$, wherein HP is a hydrophilic radical and LP is a lipophilic radical. D, D', and D'' are difunctional siloxy units substituted with methyl, hydrogen, a lipophilic radical, a hydrophilic radical or mixtures thereof In this general formula:

x=0–5000, preferably 1–1000 y=0–5000, preferably 1–1000, and z=0–5000, preferably 0–1000, with the proviso that the compound contains at least one lipophilic radical and at least one hydrophilic radical. Examples of these polymers are disclosed in U.S. Pat. No. 4,698,178, which is hereby incorporated by reference.

Particularly preferred is a linear silicone of the formula:

$$MD_xD'_yD''_zM$$

wherein $M = RRRSiO_{1/2}$ $D$ and $D' = RR'SiO_{2/2}$ $D'' = RRSiO_{2/2}$ x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein

M=trimethylsiloxy $D = Si[(CH_3)][(CH_2)_n CH_3]O_{2/2}$ where n=1–40, $D' = Si[(CH_3)][(CH_2)_o-O-PE)]O_{2/2}$ where PE is $(-C_2H_4O)_a(-C_3H_6O)_bH$, o=0–40, a=1–100 and b=1–100, and $D'' = Si(CH_3)O_{2/2}$ Typical examples of preferred organosiloxane emulsifiers in accordance with the invention include those set forth below:

I.

$$CH_3-Si(CH_3)(CH_3)-O-[Si(CH_3)(LP)-O]_x-[Si(CH_3)(HP)-O]_y-[Si(CH_3)(CH_3)-O]_z-Si(CH_3)_2-CH_3$$

II.

$$CH_3-Si(CH_3)(LP)-O-[Si(CH_3)(HP)-O]_y-[Si(CH_3)(CH_3)-O]_z-Si(CH_3)_2-CH_3$$

III.

$$CH_3-Si(CH_3)(HP)-O-[Si(CH_3)(LP)-O]_x-[Si(CH_3)(CH_3)-O]_z-Si(CH_3)_2-CH_3$$

IV.

$$CH_3-Si(CH_3)(HP)-O-[Si(CH_3)(CH_3)-O]_z-Si(CH_3)_2-LP$$

V.

(cage silsesquioxane structure with HP, CH₃, Si(CH₃)₃, and Si(CH₃)₂LP substituents)

wherein

LP is a lipophilic radical

HP is a hydrophilic radical x is 0–5000 y is 0–5000, and z is 0–5000, with the proviso that the organosiloxane contains at least on hydrophilic radical and at least one lipophilic radical.

More preferred are compounds of the generic formula I wherein LP is a lipophilic radical which is a $C_{1-40}$ straight or branched chain alkyl, HP is a hydrophilic radical containing hydroxy-polyethyleneoxy, and z is at least 1. Most preferred is a compound of the formula:

$$CH_3-Si(CH_3)_2-O-\left[Si(CH_3)((CH_2)_p CH_3)-O\right]_x-\left[Si(CH_3)((CH_2)_3-O-PE)-O\right]_y-\left[Si(CH_3)_2-O\right]_z-Si(CH_3)_3$$

wherein p is 10–40, preferably 12–20, most preferably 15, and

PE is $(-C_2H_4O)_a(-C_3H_6O)_b-H$ where x, y, z, a, and b are such that the maximum molecular weight of the polymer is approximately 50,000. Organosiloxane polymers useful in the compositions of the invention are commercially available from Goldschmidt Corporation under the ABIL tradename. The preferred polymer is cetyl dimethicone copolyol and has the tradename ABIL WE 09 or ABIL WS 08. The cetyl dimethicone copolyol may be used alone or in conjunction with other non-silicone organic emulsifiers. Preferred is where the cetyl dimethicone copolyol is in an admixture with other non-silicone organic emulsifiers and emollients. In particular, blends of 25–50% of the organosiloxane emulsifier, 25–50% of a non-silicone organic emulsifier, and 25–50% by weight emollients or oils are preferred. For example, the mixtures identified by the C.T.F.A. names cetyl dimethicone copolyol (and) polyglyceryl 4-isostearate (and) hexyl laurate, or cetyl dimethicone copolyol (and) polyglyceryl-3 oleate (and) hexyl laurate both work well. These blends contain approximately 25–50% of each ingredient, for example ABIL WE 09 contains approximately, by weight of the total ABIL composition, 25–50% cetyl dimethicone copolyol, 25–50%, polyglyceryl 4-isostearate, and 25–50% of hexyl laurate which is an emollient or oil.

Another type of preferred organosiloxane emulsifier suitable for use in the compositions of the invention are emulsifiers sold by Union Carbide under the Silwet™ trademark. These emulsifiers are represented by the following generic formulas:

$$(Me_3Si)_{y-2}[(OSiMe_2)_{x/y}O-PE]_y$$

wherein $PE = -(EO)_m(PO)_n R$

R=lower alkyl or hydrogen

Me=methyl

EO is polyethyleneoxy

PO is polypropyleneoxy m and n are each independently 1–5000 x and y are each independently 0–5000, and $$Me_3SiO(Me_2SiO)_x(MeSiO)_y SiMe_3$$
$$\phantom{Me_3SiO(Me_2SiO)_x(Me}|$$
$$\phantom{Me_3SiO(Me_2SiO)_x(Me}PE$$

wherein $PE = -CH_2CH_2CH_2O(EO)_m(PO)_n Z$

Z=lower alkyl or hydrogen, and

Me, m, n, x, y, EO and PO are as described above, with the proviso that the molecule contains a lipophilic portion and a hydrophilic portion. Again, the lipophilic portion can be supplied by a sufficient number of methyl groups on the polymer backbone.

Particularly preferred is a Silwet™ polymer of the following general formula:

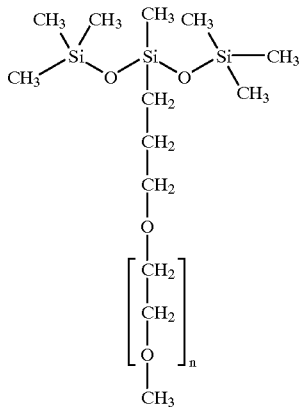

Wherein n is 1–10, preferably 8.

Another preferred organosiloxane emulsifier for use in the compositions of the invention is dimethicone copolyol.

Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABEL B-9806, as well as those sold by Rhone-Poulenc under the Alkasil tradename. Also, organosiloxane emulsifiers sold by Amerchol under the Amersil tradename, including Amersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

Other Ingredients

Waxes

The cosmetic compositions of the invention generally contain from about 1–40%, preferably 1–30%, more preferably 2–25% by weight of a cosmetically acceptable natural or synthetic wax. An acceptable wax can be a solid or semi-solid wax having a melting point of 30 to 120° C. and generally includes animal waxes, plant waxes, mineral waxes, silicone waxes, and petroleum waxes. Examples of waxes in accordance with the invention include bayberry, beeswax, candelilla, carnauba, ceresin, cetyl esters, hydrogenated jojoba oil hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, polyethylene, stearoxy dimethicone, dimethicone behenate, stearyl dimethicone, and the like.

Oils

The cosmetic compositions of the invention may also contain about 0.1–30, preferably 0.5–25, more preferably 1–20% by weight of a cosmetically acceptable oil. The oils are nonvolatile, and have a viscosity ranging from 0.5 to 1,000,000 centistokes, preferably 25 to 600,000 centistokes at 25° C. Examples of such oils include essential oils, esters, the glyceryl esters of fatty acids, fatty acids, fatty alcohols, and the like. Generally esters are of the general formula RCO—OR' wherein R and R' are each independently a straight or branched chain $C_{1-50}$ alkyl, alkenyl, or alkoxyalkyl (e.g., poly(alkyleneoxy)alkyl). One or both of R and R' is a alkyl or alkenyl, e.g. of 1 to 50 carbon atoms. Examples of suitable esters include acetyl trialkyl citrates, acetylated glycol stearate, cetearyl derivatives, cetyl acetate, cetyl acetyl ricinoleate, cetyl isononanoate, cetyl lactate, cetyl myristate, cetyl octanoate, cetyl oleate, cetyl palmitate, cetyl stearate, hexyl laurate, glycol stearate, glycol palmitate, isostearyl isostearate, jojoba oil, jojoba esters, isostearyl neopentanoate, isostearyl lactate, isostearyl isononanoate, lauryl lactate, lauryl stearate, tridecyltrimellitate, myreth derivatives, myristyl derivatives, polyethylene glycol ester derivatives, sucrose derivatives, and so on. Further examples of such esters are disclosed on pages 503 to 506 of the C.T.F.A. Cosmetic Ingredient Handbook, Third Edition, 1993, which is hereby incorporated by reference.

The nonvolatile oil may also comprise high viscosity oils which generally have a viscosity of 100,000 to 250,000 centistokes at 25° C. Examples of such oils include castor oil, lanolin, lanolin derivatives, triisocetyl citrate, $C_{10-18}$ triglycerides, caprylic/capric triglycerides, coconut oil, corn oil, cottonseed oil, hydrogenated castor oil, linseed oil, mink oil, palm oil, olive oil, illipe butter, rapeseed oil, soybean oil, sunflower seed oil, tallow, tricaprin, trihydroxystearin, triiostearin, trilaurin, trilinolein, trimyristin, triolein, tripalmitin, tristearin, tribehenin, walnut oil, wheat germ oil, cholesterol, and the like.

Also suitable as the oil component are ester derivatives such as acetylated castor oil PEG castor oils, PEG glyceryl oleates, PEG glyceryl stearates, PEG glyceryl tallowates and mixtures thereof.

Also suitable as the nonvolatile oil are various nonvolatile paraffinic hydrocarbons such as polyisobutene, mineral oil, polydecene, squalene, petrolatum, liquid polyalphaolefins such as those marketed by Henkel under the tradename Emery 3004 PAO, and the like.

Other examples of nonvolatile oils are various lanolin derivatives such as acetylated lanolin alcohol, acetylated lanolin ricinoleate, lanolin phosphates and acetates, lanolin acid, lanolin linoleate, PEG hydrogenated lanoins, and the like.

Nonvolatile nonfluorinated silicones are also suitable. Such silicones generally have a viscosity of 35 to 600,000 centistokes, preferably 50 to 100,000 centistokes, at 25° C. Examples of such silicones include amodimethicone, dimethicone, dimethicone copolyol, dimethiconol, hexadecyl methicone, methicone, phenyl trimethicone, simethicone, dimethylhydrogensiloxane, stearoxy dimethicone, vinyl dimethcicone and the like.

Fluorinated oils such as fluorinated silicones, fluroinated perfluoropolyethers, and fluorguerbet citrate esters are also suitable. Examples of suitable fluorosilicones are trimethylsilyl endcapped fluorosilicone oils, polytrifluoropropylmethylsiloxanes, and similar silicones. Perfluoropolyethers like those disclosed in U.S. Pat. Nos. 5,183,589, 4,803,067, and 5,183,588, all of which are incorporated by reference, are also suitable. These perfluoropolyethers are commercially available from Montefluos under the tradename Fomblin. Preferred are fluoroguerbet citrate esters and fluorinated derivatives of oils such as a developmental ester L6 1125A marketed by Siltech of Norcross, Ga., which is tentatively named fluoro-octododecyl meadowfoamate and is sold under the tradename Silube GME-F.

Pigments and Powders

The composition of the invention may contain 5–50%, preferably 7–45%, more preferably 10–40%, by weight of the total composition, of dry particulate matter having a particle size of 0.02 to 200, preferably 0.5 to 100, microns. The particulate matter may be colored or non-colored (for example white). Suitable powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

The powder component also may comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof.

Preferably the composition will contain both pigment and non-pigmented powders. Obviously the percentage of pigments used in the powder component will depend on the type of cosmetic being formulated. Color cosmetics generally have a much higher concentration of color than other types of cosmetics. Generally the weight ratio of pigment to non-pigmented powder will range from 1:20 to 20:1.

Preferred anhydrous stick cosmetic compositions in accordance with the invention comprise, by weight percent:
a) 10–70% of a volatile solvent,
b) 0.1–40% of a polymeric organosiloxane emulsifier containing at least one lipophilic radical and at least one hydrophilic radical,
c) 1–40% of a wax having a melting point of 30 to 120° C.,
d) 0.1–30% oil, and
e) 5–50% dry particulate matter.

In a preferred embodiment, it is desireable that the anhydrous stick composition of the invention contain 0.01–20%, preferably 0.01–15%, more preferably 0.1–10%, of a nonionic surfactant or emulsifier that co-operates with the organosiloxane emulsifier to cause the film to be more homogeneous. It is believed that the homogeneity of the film aids in producing a semi-matte finish. Suitable nonionic surfactants include abietic acid, almond oil PEG esters, beheneth 5–20, ceteareth 2–18, ceteth 1–16, choleth 10–24, coceth 3–10, pareth, nonoxynol, glyceryl derivatives such as glyceryl behenate, glyceryl caprylate, glyceryl caprylate/ caprate, glyceryl cocoate, glyceryl lanolate, glyceryl oleate, isodeceth, laureth, octoxynol, oleth, PEG derivatives, poloxamines, poloxamers, polyglyceryl derivatives, polysorbates, PPG derivatives, etc. Further examples of such nonionic surfactants are set forth on pages 588 to 592 of the C.T.F.A. Cosmetic Ingredient Handbook, Third Edition, 1993, which is hereby incorporated by reference. Preferred are polyglyceryl derivatives, and in particular polyglyceryl4-isostearate and polyglyceryl-3-oleate.

A more preferred embodiment of the invention comprises anhydrous lipstick compositions comprising, by weight percent:
a) 10–70% cyclomethicone,
b) 0.5–20% cetyl dimethicone copolyol,
c) 0.1–40% of a wax having a melting point of 30 to 120° C.,
d) 0.1–30% oil,
e) 5–50% of a dry particulate matter that comprises pigments, powders, or mixtures thereof, having a particle size of 0.02 to 100 microns, and
f) 0.01–10% of a nonionic surfactant.

Other Polymers

It may also be desired to add other polymeric materials that enhance adhesion of the stick cosmetic composition to the skin. If such polymeric materials are used, a range of 0.1–20%, preferably 0.5–15%, more preferably 1–10%, is suggested. Examples of such polymers include various types of polypropylenes as described in U.S. Pat. No. 5,302,380 which is hereby incorporated by reference.

Other polymers that can enhance adhesion to skin include silicone esters comprising units of the general formula $R_a R^E_b SiO_{[4-(a+b)/2]}$ or $R^{13}_x R^E_y SiO_{1/2}$, wherein R and $R^{13}$ are each independently an organic radical such as alkyl, cycloalkyl, or aryl, or, for example, methyl, ethyl, propyl, hexyl, octyl, decyl, aryl, cyclohexyl, and the like, a is a number ranging from 0 to 3, b is a number ranging from 0 to 3, a+b is a number ranging from 1 to 3, x is a number from 0 to 3, y is a number from 0 to 3 and the sum of x+y is 3, and wherein $R^E$ is a carboxylic ester containing radical. Preferred $R^E$ radicals are those wherein the ester group is formed of one or more fatty acid moieities (e.g. of about 2, often about 3 to 10 carbon atoms) and one or more aliphatic alcohol moieities (e.g. of about 10 to 30 carbon atoms). Examples of such acid moieities include those derived from branched-chain fatty acids such as isostearic, or straight chain fatty acids such as behenic. Examples of suitable alcohol moieties include those derived from monohydric or polyhydric alcohols, e.g. normal alkanols such as n-propanol and branched-chain etheralkanols such as (3,3,3-trimethylolpropoxy)propane. Preferably the ester subgroup (i.e. the carbonyloxy radical) will be linked to the silicon atom by a divalent aliphatic chain that is at least 2 or 3 carbon atoms in length, e.g. an alkylene group or a divalent alkyl ether group. Most preferably that chain will be part of the alcohol moiety, not the acid moiety.

Preferably the silicone ester will have a melting point of no higher than about 90° C. It can be a liquid or solid at room temperature. Preferably it will have a waxy feel and a molecular weight of no more than about 100,000 daltons.

Silicone esters having the above formula are disclosed in U.S. Pat. Nos. 4,725,658 and U.S. Pat. No. 5,334,737, which are hereby incorporated by reference. Preferred silicone esters are the liquid siloxy silicates disclosed in U.S. Pat. No. 5,334,737, e.g. diisostearoyl trimethylolpropane siloxysilicate (prepared in Examples 9 and 14 of this patent), and dilauroyl trimethylolpropane siloxy silicate (prepared in Example 5 of the patent), which are commercially available from General Electric under the tradenames SF 1318 and SF 1312, respectively.

Also suitable as the polymer components are materials such as PVP, PVP eicosene copolymer, polyvinylidene copolymer, and the like.

It may also be desirable to add other ingredients such as preservatives, antioxidants, emollients, and so on. If preservatives are added, 0.001–5%, preferably 0.01–3%, more preferably 0.1–2%, by weight of the total composition is suggested.

The invention will be further described in connection with the following examples which are set forth for the purpose of illustration only.

EXAMPLE 1

A semi-matte transfer resistant lipstick was made as follows:

|  | w/w % | |
|---|---|---|
|  | Q | S |
| PVP/eicosene copolymer | 3.00 | 3.00 |
| Synthetic hydrocarbon (mineral oil)* | 3.00 | 3.00 |
| D&C Red 7 Calcium Lake | 1.23 | 1.23 |
| D&C Red 6 Barium Lake | 2.80 | 2.80 |
| Red iron oxide | 1.01 | 1.01 |
| Cetyl dimethicone copolyol and polyglyceryl-4-isostearate and hexyl laurate (ABIL WE 09) | 4.05 | 4.05 |
| Diisostearoyl trimethylolpropane siloxy silicate | 0.91 | 0.91 |
| Synthetic wax | 7.00 | 7.00 |
| Ceresin | 1.10 | 1.10 |
| Methylparaben | 0.30 | 0.30 |
| Propylparaben | 0.10 | 0.10 |
| BHA | 0.10 | 0.10 |
| Vitamin E acetate | 0.10 | 0.10 |
| Apple extract/hydrogenated vegetable oil | 0.50 | 0.50 |
| Retinyl palmitate, cholesterol, corn oil | 0.10 | 0.10 |
| Atactic polypropylene | 0.50 | 0.50 |
| Soybean oil | 0.50 | 0.50 |
| Fluoro-octyldodecyl meadowfoamate** | 4.00 | 4.00 |
| Pentaerythritol tetraoctanoate | 1.70 | 1.70 |
| Cyclomethicone | 50.00 | 50.00 |
| Titanium dioxide/mica | 3.50 | 3.50 |
| Barium sulfate/mica/titanium dioxide | 4.00 | 4.00 |
| Mica/silica | 11.80 |  |
| Mica/dimethicone |  | 11.80 |

*Emery 3004 PAO, Henkel Corporation, Emery Group. (liquid polyalphaolefin having the chemical name synthetic aliphatic hydrocarbon)
**Silube GME-F, Developmental Ester L61125A - Siltech, Norcross Georgia The liquid ingredients, other than the cyclomethicone, were mixed. The pigments and other powders were added. The wax materials were combined and heated to a molten mass, and then added to the liquid material with mixing. After complete mixing, the molten mass was poured into the desired containers and allowed to cool. The lipstick provided a semi-matte finish to the lips when applied and was transfer resistant.

EXAMPLE 2

A transfer resistant lipstick with semi-matte finish was made as follows:

|  | w/w % |
|---|---|
| PVP eicosene copolymer | 3.00 |
| Synthetic hydrocarbon* | 3.50 |
| Fluoro-octododecyl meadowfoamate** | 4.00 |
| Synthetic wax | 7.00 |
| Ozokerite | 1.00 |
| Ceresin | 1.10 |
| Methyl paraben | 0.30 |
| Propyl paraben | 0.10 |
| BHA | 0.10 |
| Vitamin E acetate | 0.10 |
| Apple extract/hydrogenated vegetable oil | 0.30 |
| Polypropylene | 0.50 |
| Aloe extract | 0.30 |
| PE 48 pentaerythritol tetraoctanoate | 1.00 |
| Diisostearoyl trimethylolpropane siloxy silicate | 1.00 |
| Silwet***silicone copolyol | 4.00 |
| D&C Red 7, Ca Lake | 1.00 |
| D&C Red 6, Ba Lake | 3.25 |
| D&C Red 27, Al Lake | 0.05 |
| FD&C Yellow 6 Al Lake | 0.05 |
| Bismuth oxychloride/mica | 5.00 |
| Mica | 2.10 |
| Cyclomethicone | 49.47 |
| Mica/silica | 11.78 |

*Emery 3004 PAO, Henkel Corporation, Emery Group. (liquid polyalphaolefin)
**Silube GME-F, Developmental Ester L61125A - Siltech, Norcross Georgia
***Silwet, Union Carbide. (polyalkylene oxide-modified dimethylpolysiloxane)

EXAMPLE 3

A transfer resistant lipstick with semi-matte finish was made as follows:

|  | w/w % |
|---|---|
| PVP eicosene copolymer | 3.00 |
| Synthetic hydrocarbon* | 3.50 |
| Fluoro-octyldodecyl meadowfoamate** | 4.00 |
| Synthetic wax | 7.00 |
| Ozokerite | 1.00 |
| Ceresin | 1.10 |
| Methyl paraben | 0.30 |
| Propyl paraben | 0.10 |
| BHA | 0.10 |
| Vitamin E acetate | 0.10 |
| Apple extract/hydrogenated vegetable oil | 0.30 |
| Polypropylene | 0.50 |
| Aloe extract | 0.30 |
| PE-48 pentaerythritol tetraoctanoate | 1.00 |
| Diisostearoyl trimethylolpropane siloxy silicate | 1.00 |
| Dimethicone copolyol*** | 5.00 |
| D&C Red 7 Ca Lake | 1.00 |
| D&C Red 6 Ba Lake | 3.25 |
| D&C Red 27 Al. Lake | 0.05 |
| FD&C yellow 6 Al. Lake | 0.05 |
| Bismuth oxychloride | 5.00 |
| Mica | 2.10 |
| Cyclomethicone | 48.47 |

The above lipstick was slightly hard, but did not transfer. When applied to skin it exhibited a semi-matte finish and a slightly sticky feel.

EXAMPLE 4

Lipsticks Q and S of Example 1 were comparatively tested against Revlon Colorstay and Alexandra DeMarkoff Lips Like Hers. Fifteen panelists were asked to apply each of Revlon Colorstay, Lipstick Q, Lipstick S and Alexandra DeMarkoff, Lips Like Hers. The panelists were asked to answer the following questions:

1. Kiss Test.

The lipsticks were applied to the lips and allowed to set for at least 60 seconds. The panelists were asked to kiss the back of their hands and answer the following:

a) Panelists who reported that the lipstick did not leave a trace of color:

| Colorstay | Lipstick Q | Lipstick S | ADM Lips Like Hers |
|---|---|---|---|
| 9 | 6 | 10 | 9 | b) Panelists who reported that the lipstick did leave a trace of color:

| Colorstay | Lipstick Q | Lipstick S | ADM Lips Like Hers |
|---|---|---|---|
| 6 | 9 | 5 | 6 |

2. Lipstick Application (desired characteristics: smooth, even, good payoff):

|  | Colorstay | Lipstick Q | Lipstick S | ADM |
|---|---|---|---|---|
| Excellent | 9 | 14 | 14 | 9 |
| Very Good | 6 | 1 | 1 | 4 |
| Good | — | — | — | 2 |
| Fair | — | — | — | — |
| Poor | — | — | — | — |

3. Feel on Lips/comfort level:

|  | Colorstay | Lipstick Q | Lipstick S | ADM |
|---|---|---|---|---|
| Excellent | 11 | 14 | 14 | 9 |
| Very good | 4 | 1 | 1 | 3 |
| Good | — | — | — | 2- |
| Fair | — | — | — | 1 |
| Poor | — | — | — | — |

EXAMPLE 5

The lipsticks Q and S of Example 1 (Sample A) were compared with a commercially available lipstick made by L'Oreal under the Colour Endure label (Sample B) to ascertain which product was more moisturizing to lips.

A total of thirteen subjects, after having refrained from using lip products for two days, were recruited for the study. Eleven subjects were used for the treatment group and two subjects served as the untreated control group. Dry lips were simulated by blowing a stream of dry air over the lips for one minute. Baseline readings were performed on the dry lips using the NOVA Dermal Phase Meter fitted with a special lip probe. Subjects applied enough product to cover the lips and were instructed to refrain from licking the lips during the study. This was a half lip study; that is, alternate sides (left vs. right) contained Sample A vs. Sample B. After fifteen minutes, sample was wiped from the lips and readings were performed.

Lip moisture improved significantly for both samples A and B at fifteen minutes after one application of product. Average lip moisture improved by 75% for sample A and 43% for Sample B. Additionally, there was directional superiority of Sample A over Sample B at the 90% confidence level. There was no significant change in untreated control sites throughout the study.

In the context of this study, both samples give lips an immediate moisture boost and there is directional superiority of the formula of Example 1 over L'Oreal Colour Endure as set forth below:

| Sample | N | % Moisture Improvement | Standard Error |
|---|---|---|---|
| Sample A[1] | 11 | 74.6* D | 21.1 |
| Sample B[2] | 11 | 43.0* D | 16.3 |
| Untreated Control | 2 | NC | NC |

[1]Lipsticks of Example 1
[2]L'Oreal Colour Endure

We claim:

1. An anhydrous cosmetic stick composition with improved transfer resistance comprising, by weight of the total composition:

(a) 10–70% cyclomethicone, (b) 0.1–40% of a polymeric organosiloxane emulsifier which is cetyl dimethicone copolyol, (c) 0.1–30% of a nonvolatile oil having a viscosity of 36 to 600,000 centistokes at 25° C. and selected from the group consisting of an ester oil, wherein the ester oil is pentaerythriol tetraoctonoate or has the formula RCO—OR' wherein R and R' are each independently a straight or branched chain C1–50 alkyl, alkenyl, or alkoxyalkyl a paraffinic hydrocarbon, wherein the paraffinic hydrocarbon is selected from the group consisting of polyisobutene, polydecene, squalene, polyalphaolefins and mixtures thereof and mixtures thereof, (d) 1–40% of a wax having a melting point of 30 to 120° C., and (e) 5–50% of dry particulate matter having a particle size of 0.02 to 200 microns.

2. The composition of claim 1 wherein the wax is selected from the group consisting of shellac wax, synthetic wax, ozokerite, and mixtures thereof.

3. The composition of claim 1 wherein the paraffinic hydrocarbon comprises polydecene.

4. The composition of claim 1 wherein R and R' are a straight or branched chain C1–50 alkyl.

5. The composition of claim 4 wherein the ester oil comprises hexyl laurate.

* * * * *